(12) United States Patent
Roth

(10) Patent No.: US 9,243,299 B2
(45) Date of Patent: Jan. 26, 2016

(54) AVIAN GROUP D ROTAVIRUS

(75) Inventor: Bernhard Roth, Lahntal (DE)

(73) Assignee: Novartis AG, Basel (CH)

( * ) Notice: Subject to any disclaimer, the term of this patent is extended or adjusted under 35 U.S.C. 154(b) by 412 days.

(21) Appl. No.: 13/582,739

(22) PCT Filed: Mar. 4, 2011

(86) PCT No.: PCT/IB2011/000600
§ 371 (c)(1),
(2), (4) Date: Feb. 21, 2013

(87) PCT Pub. No.: WO2011/107883
PCT Pub. Date: Sep. 9, 2011

(65) Prior Publication Data
US 2013/0216567 A1   Aug. 22, 2013

(30) Foreign Application Priority Data

Mar. 4, 2010 (GB) .................................. 1003630.9

(51) Int. Cl.
| | |
|---|---|
| *C07H 21/04* | (2006.01) |
| *C12Q 1/70* | (2006.01) |
| *A61K 39/15* | (2006.01) |
| *C07K 14/005* | (2006.01) |
| *C07K 7/06* | (2006.01) |
| *C07K 7/08* | (2006.01) |
| *C07K 14/14* | (2006.01) |
| *G01N 33/68* | (2006.01) |
| *A61K 39/12* | (2006.01) |
| *A61K 39/00* | (2006.01) |

(52) U.S. Cl.
CPC ................ *C12Q 1/701* (2013.01); *A61K 39/12* (2013.01); *A61K 39/15* (2013.01); *C07K 7/06* (2013.01); *C07K 7/08* (2013.01); *C07K 14/005* (2013.01); *C07K 14/14* (2013.01); *C12Q 1/70* (2013.01); *G01N 33/6893* (2013.01); *A61K 39/00* (2013.01); *C12N 2720/12322* (2013.01); *C12N 2720/12334* (2013.01)

(58) Field of Classification Search
None
See application file for complete search history.

(56) References Cited

U.S. PATENT DOCUMENTS 6,187,319 B1   2/2001   Herrmann et al.

OTHER PUBLICATIONS

EMBL database accession No. GU733448. Trojnar et al. (Sep. 20, 2010). "Rotavirus D chicken/05V0049/DEU/2005 segment 6, complete sequence."
Otto et al. (2006). "Detection of rotaviruses and intestinal lesions in broiler chicks from flocks with runting and stunting syndrome (RSS)," Avian Dis. 50(3):411-8.
Schumann et al. (2009). "Evidence of interspecies transmission and reassortment among avian group A rotaviruses," Virology 386(2):334-43.
Trojnar et al. (2010). "The Genome Segments of a Group D Rotavirus Possess Group A-Like Conserved Termini but Encode Group-Specific Proteins," J. Virol. 84(19): 10254-10265.
International Search Report mailed on Aug. 5, 2011, for International Patent Application No. PCT/IB2011/000600, filed on Mar. 4, 2011.
EMBL database accession No. ATL99214 ("Human VP6"). Wang et al. (Aug. 20, 2008).
EMBL database accession No. GQ477133 ("Human rotavirus A isolate Nov09-KZ inner capsid protein (VP6) gene complete cds"). Zhirakovskaya et al. (Sep. 23, 2009).
NCBI database accession No. AB008672 ("Human rotavirus C mRNA for VP6, complete cds"). Wu et al. (Feb. 15, 2008).
NCBI database accession No. AY786570 ("Human rotavirus C strain V460 major inner capsid protein VP6 (VP6) gene, complete cds"). Barman et al. (Nov. 1, 2005).
NCBI database accession No. Q6PMI4 ("Intermediate capsid protein VP6"). McNeal et al. (Apr. 14, 2009).
Aucouturier et al. (2001). "Adjuvants designed for veterinary and human vaccines," Vaccine 19(17-19):2666-72.
Lipman et al. (2005). "Monoclonal versus polyclonal antibodies: distinguishing characteristics, applications, and information resources," ILAR J. 46(3):258-68.
Zauner et al. (2013). "Glycoproteomic analysis of antibodies," Mol Cell Proteomics, 12(4):856-65.

*Primary Examiner* — Michelle S Horning
(74) *Attorney, Agent, or Firm* — Morrison & Foerster LLP

(57) ABSTRACT

The invention relates to a newly identified avian rotavirus D VP6 nucleotide sequence and uses thereof.

12 Claims, 3 Drawing Sheets

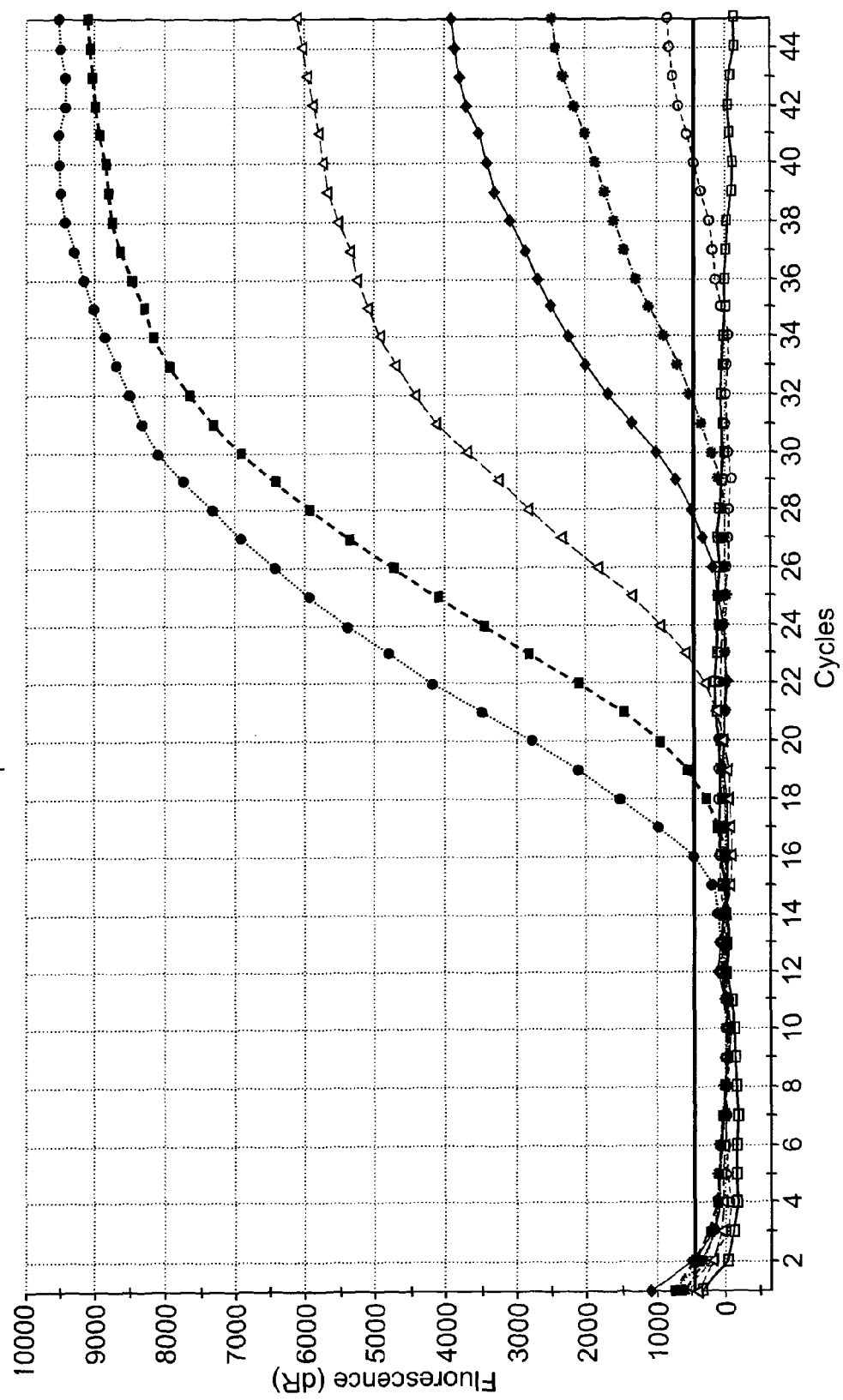

FIG. 2

```
CLUSTAL 2.0.12 multiple sequence alignment seq_id_1    ------------------------------------------------------------
seq_id_2    ATGGAGGCGCTGTCTTCAATTGCGTTGACTGTCAGAGAAGCACGAGAAAAGATCATAAAT  60 seq_id_1    ------------------------------------------------------------
seq_id_2    GGAACAATATATTCCAACGTGTCGGATGTAATACAACAATTCAATCAAATGGTTAGAGTA  120 seq_id_1    ------------------------------------------------------------
seq_id_2    TTGAATGGATCAACTTTTACTACTGGTGGATTGGCTACTATGCCACTTAGAGAATGGACT  180 seq_id_1    ------------------------------------------------------------
seq_id_2    TTTGATCTGCCGCAATTGGGTACAACTTTACTAAATATAGATGCTAATTATGTAGAATCA  240 seq_id_1    ------------------------------------------------------------
seq_id_2    ATGACACCAACACTTGATATGTTGACTGAGTTTGTGATTGCTGTATGTGAAACTGAGTTG  300 seq_id_1    ------------------------------------------------------------
seq_id_2    CTAGTTGATAACAATAGAAATGGTGCATACCCACAATCTGAAGCATTGAGATTACTATCT  360 seq_id_1    ------------------------------------------------------------
seq_id_2    AACAATAAATATGTTTTCCTTAATATGGATTTAGGATCTAAGTACATNTCAGAATGGCAT  420 seq_id_1    ------------------------------------------------------------
seq_id_2    TATAGATTGTCAGCTAGGGATCCAATGTTTTCAAATCATGTACCATATATATTCCCATAT  480 seq_id_1    ------------------------------------------------------------
seq_id_2    GATATGGCTATAGCATATGATAGAGTAACGGCTGCTTACGATAATGTGTCAGGAACACGA  540 seq_id_1    ------------------------------------------------------------
seq_id_2    TTTGCATCACTAAATAATGCTATACATTTTGCTGCATTTGATCAAGACTTTGTTCGTGGA  600 seq_id_1    ------------------------------------------------------------
seq_id_2    CAGCCAGCTAATGCGAGGCAATTTGAATACCTTTACAATTTGAGGACGCCAGTGTCTAAT  660 seq_id_1    ------------------------------------------------------------
seq_id_2    GCTACTATAGTCATACATCCAATATCAGANATTTTGTCAGTACCAAGTATGATTAGAAAC  720 seq_id_1    ------------------------------------------------------------
seq_id_2    CAAGCTGCCACACACTATTGGCCATACAACCCATATAATATACCGACGTTTAGAGATGAC  780 seq_id_1    ------------------------------------------------------------
seq_id_2    ATTAGAGTTGAATTCCAACTTGCAGGACAAGTAATATATGTAGCTGCGAATCTGGGAATG  840 seq_id_1    ------------------------------------------------------------
seq_id_2    CATACTATTCCGCAATTTGATGCAGTAAATATCATCTTGACAATGAGGAGATTGCCATTG  900 seq_id_1    ------------------------------------------------------------
seq_id_2    CTAGCTGATTTGCAAAATATATTCCCAGCTGGAAATCCATCAGCAACACATCAAGCTGTA  960 seq_id_1    -------------------------------GCGACAACTGAGACAACTGTGCCATCTATTAAT  33
seq_id_2    ATTTCAACTAAAATTGAAGTGCTGAATGCGACAACTGAAACAACTGTACCATCTATTGAT  1020
                                           ********  **** **** seq_id_1    GAACATTTGTATGCTTTAATTGTAGGAACTAGAGGTAGATATCAGATGCAGGCTGGACCA  93
seq_id_2    GAACATTTGTATGCTTTAATTGTAGGAACTAGAGGTAGATATCAGATGCAGGCTGGACCA  1080
            ************************************************************ seq_id_1    GTCTTTCCTCCTGGTATGCGTTGGGATGATATTCTGAATAGGTATACACCAGCGAGACAA  153
seq_id_2    GTCTTTCCTCCTGGTATGCGTTGGGATGATATTCTGAATAGGTATACACCAGCAAGACAA  1140
            ***************************************************** **** seq_id_1    TCTAATATGCAACGGTTGATGACAACTGCTTCCATACTTGATCTAGTTTCCATGTAGGCG  213
seq_id_2    TCTAATATGCAACGGTTGATGACAACTGCTTCCATACTTGATCTAGTTTCCATG------  1194
            ****************************************************** seq_id_1    CGGAAGATGCCACTCGAGATAACATCAAGGTTAAAATACGTGGAACTAGGCTGAGTATGT  273
seq_id_2    ------------------------------------------------------------ seq_id_1    GGCACAGTAATGCGGAGTAATATCTGCATGGAAGAAATCTGTTATCATACGTCAGCAGCT  333
seq_id_2    ------------------------------------------------------------ seq_id_1    ATTATCTTTGACCGGATCCCGGGAATTCGG  363
seq_id_2    ------------------------------
```

FIG. 3

CLUSTAL 2.0.12 multiple sequence alignment

```
SEQ_ID_3    ------------------------------------------------------------
SEQ_ID_4    MEALSSIALTVREAREKIINGTIYSNVSDVIQQFNQMVRVLNGSTFTTGGLATMPLREWT 60

SEQ_ID_3    ------------------------------------------------------------
SEQ_ID_4    FDLPQLGTTLLNIDANYVESMTPTLDMLTEFVIAVCETELLVDNNRNGAYPQSEALRLLS 120

SEQ_ID_3    ------------------------------------------------------------
SEQ_ID_4    NNKYVFLNMDLGSKYXSEWHYRLSARDPMFSNHVPYIFPYDMAIAYDRVTAAYDNVSGTR 180

SEQ_ID_3    ------------------------------------------------------------
SEQ_ID_4    FASLNNAIHFAAFDQDFVRGQPANARQFEYLYNLRTPVSNATIVIHPISXILSVPSMIRN 240

SEQ_ID_3    ------------------------------------------------------------
SEQ_ID_4    QAATHYWPYNPYNIPTFRDDIRVEFQLAGQVIYVAANLGMHTIPQFDAVNIILTMRRLPL 300

SEQ_ID_3    ---------------------------ATTETTVPSINEHLYALIVGTRGRYQMQAGP 31
SEQ_ID_4    LADLQNIFPAGNPSATHQAVISTKIEVLNATTETTVPSIDEHLYALIVGTRGRYQMQAGP 360
                                       ********* *********************

SEQ_ID_3    VFPPGMRWDDILNRYTPARQSNMQRLMTTASILDLVSM 69
SEQ_ID_4    VFPPGMRWDDILNRYTPARQSNMQRLMTTASILDLVSM 398
            *************************************
```

AVIAN GROUP D ROTAVIRUS

CROSS REFERENCE TO RELATED APPLICATIONS

This application is a U.S. National Phase patent application of PCT/IB2011/000600, filed Mar. 4, 2011, which claims priority to United Kingdom patent application Serial No. 1003630.9, filed Mar. 4, 2010, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 223002125800SubSeqListing.txt, date recorded: Apr. 17, 2013, size: 13KB).

TECHNICAL FIELD

Avivan Group D Rotavirus

BACKGROUND ART

Rotaviruses belong to the Reoviridae family of viruses, and can affect the gastrointestinal system and the respiratory tract of birds, amongst other organisms. The family of Reoviridae consists of different genera including *orthoreovirus* (avian and mammalian reoviruses), *orbivirus* (Bluetongue virus) and *rotavirus* (groups A to G).

Rotaviruses are non-enveloped, double-shelled RNA viruses. The genome is composed of 11 segments of double-stranded RNA, which code for six structural and six non-structural proteins.

There are six viral proteins (VPs) that form the three-layered icosahedral protein capsid of the virion. These structural proteins are called VP1, VP2, VP3, VP4, VP6 and VP7 [1]. VP6 forms the bulk of the capsid. It is highly antigenic and can be used to identify rotavirus species [2]. In addition to the VPs, there are six non-structural proteins (NSPs) that are only produced in cells infected by rotavirus. These are called NSP1, NSP2, NSP3, NSP4, NSP5 and NSP6 [1].

Avian rotaviruses (ARVs) are well known [3, 4 and 5] and frequently affect poultry flocks, and in particular chicken flocks, worldwide. The symptoms in infected chicken are diarrhoea with subsequent slow weight gain, a syndrome which is known as Malabsorption Syndrome (MAS) or Runting Stunting Syndrome (RSS).

In one field study, broiler chicks between 6 and 18 days of age from 8 flocks with RSS were examined to determine which ARVs are major contributors to the pathogenesis of RSS [6]. In this study, ARVs were detected in 32 of 34 chicks from the flocks with RSS. Four groups of ARVs were identified in flocks with RSS: AVR A, D, F and G. The results of this study showed that group D ARV plays a major role in the pathogenesis of RSS.

The economic impact of RSS on chicken breeders is severe. All infected chickens will be lost. Early detection and prevention of infection by ARV is therefore highly desirable.

Currently, ARVs are usually detected and identified on the basis of the migration of the 11 genomic RNA fragments using RNA-PAGE. The RNA-PAGE pattern characteristic of an group D ARV is 5:2:2:2 [7]. This characteristic pattern of RNA migration can be used to identify group D ARVs.

ARVs can also be detected using ELISA [8], transmission electron microscopy, and reverse-transcriptase polymerase chain reaction (RT-PCR) [6]. Only PAGE allows discrimination of different ARV groups, but it has only a low degree of sensitivity. At present, PCR methods are only available for detection of group A rotaviruses. No nucleotide sequence data existed for group D ARVs at the priority date. There is therefore a pressing need to develop alternative methods of the detection of other rotaviruses, and in particular group D rotaviruses. In particular, there is a pressing need to develop a rapid and sensitive detection method for group D ARVs.

DISCLOSURE OF THE INVENTION

The present invention relates to the identification of a new group D avian rotavirus (ARVD) [9] and offers several opportunities in veterinary and pharmaceutical fields. The invention provides:

- The sequence of the nucleic acid encoding the VP6 polypeptide, and fragments and variants thereof, and nucleic acids complementary to the nucleic acid encoding the VP6 polypeptide.
- The VP6 polypeptide sequence encoded by the nucleic acids mentioned above, and fragments, variants and antigenic fragments thereof.
- Nucleic acid molecules which hybridizes under high stringency conditions with the nucleic acid encoding the VP6 polypeptide, including primers and probes.
- Antibodies that bind to the VP6 polypeptide, fragments, variants, and/or antigenic determinants thereof.
- Diagnostic reagents and kits comprising such reagents for identifying the presence or absence of a ARVD in a biological sample and methods which can be used to diagnose ARVD infection or identify the presence or absence of an ARVD virus in a biological sample.
- Vaccines for the treatment of or protection from ARVD infection.
- Methods of verifying that eggs, in particular embryonated eggs for vaccine production, are ARVD-free.

Nucleic Acid

The invention provides a nucleic acid comprising the nucleotide sequence of SEQ ID NO: 1 or SEQ ID NO: 2. The invention also provides a nucleic acid comprising a nucleotide sequence having at least i % identity to SEQ ID NO: 1 or SEQ ID NO: 2. The value of i can be selected from 75%, 80%, 85%, 90%, 95%, 96%, 97%, 98%, 99%, 99.5%, 99.9%. Sequence identity should be calculated along the entire length of the nucleotide sequence.

SEQ ID NO: 2 provides the entire ARVD VP6 coding sequence. SEQ ID NO: 1 provides a nucleic acid comprising a fragment of the VP6 coding sequence as recited in SEQ ID NO 2, and further comprising a 3' untranslated sequence.

Preferably, the nucleic acid encodes an ARVD VP6 polypeptide. The nucleic acids of the invention may encode an ARVD VP6 polypeptide as recited in SEQ ID NO: 3 or SEQ ID NO: 4.

The invention also encompasses fragments of the nucleic acid sequences as recited in SEQ ID NO: 1 and/or 2. Thus the invention provides a nucleic acid comprising a fragment of at least n consecutive nucleotides of SEQ ID NOs: 1 and/or 2, wherein n is 8, 9, 10, 11, 12, 13, 14, 15, 16, 17, 18, 19, 20, 21, 22, 23, 24, 25, 30, 35, 40, 50 or more. The nucleic acid may have a total length of n+x nucleotides, wherein x=0, 1, 2, 3, 4, 5, 6, 7, 8, 9, 10, 11, 12, 13, 14, 15, 16, 17, 18, 19, 20, 21, 22, 23, 24, 25, 30, 35, 40, 50 or more. In one embodiment, the value of n is 24.

In a further embodiment, the invention provides a nucleic acid comprising the reverse complement of SEQ ID NO: 1 or SEQ ID NO: 2. The invention also provides a nucleic acid comprising a nucleic acid sequence that is at least 75%, 80%, 85%, 90%, 95%, 96%, 97%, 98%, 99%, 99.5%, 99.9% identical or greater to the reverse complement of the nucleic acid sequence as recited in SEQ ID NO: 1 or SEQ ID NO: 2. The invention also provides a nucleic acid comprising a fragment consists of at least n consecutive nucleotides derived from the reverse complement of SEQ ID NOs: 1 and/or 2, wherein n is 8, 9, 10, 11, 12, 13, 14, 15, 16, 17, 18, 19, 20, 21, 22, 23, 24, 25, 30, 35, 40, 50 or more. The nucleic acid may have a total length of n+x nucleotides, wherein x=0, 1, 2, 3, 4, 5, 6, 7, 8, 9, 10, 11, 12, 13, 14, 15, 16, 17, 18, 19, 20, 21, 22, 23, 24, 25, 30, 35, 40, 50 or more. In one embodiment, the value of n is 10.

In a further embodiment, the invention provides a nucleic acid which hybridizes under stringent conditions to a nucleic acid consisting of SEQ ID NO: 1 and/or SEQ ID NO: 2. Exemplary stringent conditions for hybridization are 0.1× SSC, 0.1% SDS at 65° C. for 10 minutes, and washed with 2×SSC, 0.1% SDS for 10 minutes followed by 0.1×SSC, 0.1% SDS for a further 10 minutes.

The invention provides nucleic acid of formula 5'-X-Y-Z-3', wherein: -X- is a nucleotide sequence consisting of x nucleotides; -Z- is a nucleotide sequence consisting of z nucleotides; -Y- is a nucleotide sequence consisting of either (a) a fragment of SEQ ID NO: 1 or 2 or (b) the complement of (a); and said nucleic acid 5'-X-Y-Z-3' is neither (i) a fragment of SEQ ID NO: 1 or 2 nor (ii) the complement of (i). The -X- and/or -Z- moieties may, for example, comprise a promoter sequence (or its complement).

The invention also provides nucleic acids which comprise the nucleic acids and fragments of the invention and which also comprise further nucleotides, modified nucleotides, or one or more detectable labels. Such nucleic acids may be useful as primers and/or probes in methods including LCR, PCR, RT-PCR, real-time PCR, real-time RT-PCR, qPCR, qRT-PCR, Northern Blotting, and Southern Blotting.

Exemplary labels include radioisotopes, fluorescent molecules, biotin, basepair mismatches, hairpin structures and the like. Many suitable fluorophores are known and can be used, include but are not limited to fluorescein, in particular 5-FAM (also called 5-carboxyfluorescein; also called Spiro (isobenzofuran-1(3H), 9'-(9H)xanthene)-5-carboxylic acid, 3',6'-dihydroxy-3-oxo-6-carboxyfluorescein); lissamine; phycoerythrin; rhodamine (Perkin Elmer Cetus); Cy2, Cy3, Cy3.5, Cy5, Cy5.5, Cy7; FluorX (Amersham) and further labels as described in reference [10]. It is within the skill of one of skill in the art of molecular biology to incorporate such labels into nucleic acid molecules. In one specific embodiment, the nucleic acid comprises a fluorescent label and a quencher. Suitable quenchers include but are not limited to 6-TAMRA (6-carboxytetramethylrhodamine; Xanthylium, 9-(2,5-dicarboxyphenyl)-3,6-bis(dimethylamino); and DABCYL (4-((4-(dimethylamino)phenyl) azo)benzoic acid). Labelling of nucleic acids with both FAM (e.g. at 5') and DABCYL (e.g. at 3') is preferred.

In a further embodiment, the invention provides a vector comprising a nucleic acid of the invention. For example, the invention includes cloning or expression vectors comprising a nucleic acid of the invention. The invention also provides vectors comprising the nucleic acids of the invention and further comprising additional nucleic acids, for example nucleic acid encoding further polypeptides, comprising promoter or terminator sequences, comprising restriction endonuclease recognition sites etc.

Nucleic acid according to the invention can take various forms (e.g. single-stranded, double-stranded, vectors, primers, probes, labeled etc.). In any of the embodiments described above, the nucleic acids and polynucleotides may be DNA, RNA, hybrid DNA/RNA molecules, and/or modified DNA or RNA, or PNA (peptide nucleic acid). The nucleic acids and polynucleotides may also comprise at least one modified sugar and/or base moiety, or may comprise a modified backbone or non-natural internucleoside linkage.

Where a nucleic acid is DNA, it will be appreciated that "U" in a RNA sequence will be replaced by "T" in the DNA. Similarly, where a nucleic acid is RNA, for example as in the genome of an ARV, it will be appreciated that "T" in a DNA sequence (such as in SEQ ID NO: 1 or SEQ ID NO: 2) will be replaced by "U" in the RNA.

The nucleic acids and polynucleotides of the invention can also be modified by chemically linking the oligonucleotide to one or more moieties or conjugates to enhance the activity, stability or detection of the oligonucleotide. Such moieties or conjugates include chromophores and fluorophores as described above, and further include lipids such as cholesterol, cholic acid, thioether, aliphatic chains, phospholipids, polyamines, polyethylene glycol (PEG), palmityl moieties, and others as disclosed in, for example, references 11 to 18.

Nucleic acids of the invention are preferably provided in purified or substantially purified form i.e. substantially free from other nucleic acids (e.g. free from naturally-occurring nucleic acids), particularly from other ARVD or host cell nucleic acids, generally being at least about 50% pure (by weight), and usually at least about 90% pure. Nucleic acids of the invention are preferably ARVD nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Polypeptides

The invention provides a polypeptide that comprises the amino acid sequence of SEQ ID NO: 3 or SEQ ID NO: 4. The invention further provides a polypeptide comprising an amino acid sequence that is at least j % identical to the polypeptide sequence as recited in SEQ ID NOs: 3 and/or 4. The value of j can be selected from 75%, 80%, 85%, 90%, 95%, 96%, 97%, 98%, 99%, 99.5% or 99.9%. Sequence identity should be calculated along the entire length of the amino acid sequence.

Preferably, the polypeptide is an ARVD VP6 polypeptide. SEQ ID NO: 3 corresponds to the polypeptide encoded by SEQ ID NO: 1 and SEQ ID NO: 4 corresponds to the polypeptide encoded by SEQ ID NO: 2. SEQ ID NOs: 3 and 4 are aligned in FIG. 3.

The invention also provides a polypeptide which comprise at least one fragment of SEQ ID NO: 3 or SEQ ID NO: 4, wherein the fragment consists of at least w consecutive amino acids of SEQ ID NO: 3 and/or SEQ ID NO: 4, wherein w is 6, 7, 8, 9, 10, 11, 12, 13, 14, 15, 16, 17, 18, 19, 20, 21, 22, 23, 24, 25, 30, 35, 40, 50 or more. The polypeptide may have a total length of w+x amino acids, wherein x=0, 1, 2, 3, 4, 5, 6, 7, 8, 9, 10, 11, 12, 13, 14, 15, 16, 17, 18, 19, 20, 21, 22, 23, 24, 25, 30, 35, 40, 50 or more.

The invention also provides variants of the polypeptides and fragments of the invention that comprise one or more amino acid substitutions, insertions or deletions. For example, SEQ ID NO: 3 is a variant of a C-terminal fragment of SEQ ID NO: 4, which contains 1 amino acid substitution (FIG. 3).

A polypeptide of the invention may, compared to SEQ ID NO: 3 or 4, include one or more (e.g. 1, 2, 3, 4, 5, 6, 7, 8, 9, 10, etc.) conservative amino acid substitutions i.e. replacements of one amino acid with another which has a related side chain. Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. Moreover, the polypeptides may have one or more (e.g. 1, 2, 3, 4, 5, 6, 7, 8, 9, 10, etc.) single amino acid deletions relative to SEQ ID NO: 3 or 4. Furthermore, the polypeptides may include one or more (e.g. 1, 2, 3, 4, 5, 6, 7, 8, 9, 10, etc.) insertions (e.g. each of 1, 2, 3, 4 or 5 amino acids) relative to SEQ ID NO: 3 or 4.

In one particular embodiment, the fragment is capable of inducing an immune response in a subject. The subject may be avian or mammalian. In one particular embodiment, the subject is a poultry bird, for example a chicken or a turkey.

The fragments may comprise at least one T-cell or, preferably, a B-cell epitope. T- and B-cell epitopes can be identified empirically (e.g. using PEPSCAN [19,20] or similar methods), or they can be predicted (e.g. using the Jameson-Wolf antigenic index [21], matrix-based approaches [22], TEPITOPE [23], neural networks [24], OptiMer & EpiMer [25,26], ADEPT [27], Tsites [28], hydrophilicity [29], antigenic index [30] or the methods disclosed in reference 31 and 32, etc.). Exemplary epitopes found in SEQ ID NO: 4 and identified by the method described in reference 32 are given in table 1.

When the polypeptide is capable of specifically binding to and anti-ARVD VP6 antibody as described herein, the polypeptide may also be referred to as an antigen. The invention includes polypeptides which are ARVD viral antigens, and polynucleotides encoding these ARVD viral antigens.

Polypeptides of the invention can be prepared in many ways e.g. by chemical synthesis (in whole or in part), by digesting longer polypeptides using proteases, by translation from RNA, by purification from cell culture (e.g. from recombinant expression), from the organism itself (e.g. after bacterial culture, or direct from patients), etc. A preferred method for production of peptides <40 amino acids long involves in vitro chemical synthesis [33,34]. Solid-phase peptide synthesis is particularly preferred, such methods based on tBoc or Fmoc [35] chemistry. Enzymatic synthesis [36] may also be used in part or in full. As an alternative to chemical synthesis, biological synthesis may be used e.g. the polypeptides may be produced by translation. This may be carried out in vitro or in vivo. Biological methods are in general restricted to the production of polypeptides based on L-amino acids, but manipulation of translation machinery (e.g. of aminoacyl tRNA molecules) can be used to allow the introduction of D-amino acids (or of other non natural amino acids, such as iodotyrosine or methylphenylalanine, azidohomoalanine, etc.) [37]. Where D-amino acids are included, however, it is preferred to use chemical synthesis. Polypeptides of the invention may have covalent modifications at the C-terminus and/or N-terminus.

Polypeptides of the invention are preferably provided in purified or substantially purified form i.e. substantially free from other polypeptides (e.g. free from naturally-occurring polypeptides), particularly from other ARVD or host cell polypeptides, and are generally at least about 50% pure (by weight), and usually at least about 90% pure i.e. less than about 50%, and more preferably less than about 10% (e.g. 5% or less) of a composition is made up of other expressed polypeptides. Polypeptides of the invention are preferably ARVD polypeptides.

Polypeptides of the invention may be attached to a solid support. Polypeptides of the invention may comprise a detectable label (e.g. a radioactive or fluorescent label, or a biotin label).

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can occur as single chains or associated chains. Polypeptides of the invention can be naturally or non-naturally glycosylated (i.e. the polypeptide has a glycosylation pattern that differs from the glycosylation pattern found in the corresponding naturally occurring polypeptide). The polypeptides of the invention may be isolated or purified.

The invention provides polypeptides comprising a sequence -X-Y- or -Y-X-, wherein: -X- is an amino acid sequence as defined above and -Y- is not a sequence as defined above i.e. the invention provides fusion proteins.

The invention provides a process for producing polypeptides of the invention, comprising the step of culturing a host cell of to the invention under conditions which induce polypeptide expression.

The invention provides a process for producing a polypeptide of the invention, wherein the polypeptide is synthesised in part or in whole using chemical means.

Methods and Kits for the Detection of ARDV Nucleic Acids

The invention also provides kits and methods for detecting the presence or absence of ARVD in biological samples. In particular, the invention provides kits and methods for the detection of the nucleic acids of the invention.

In a particular embodiment, the invention provides a kit comprising primers for amplifying a template sequence contained within a nucleic acid of the invention, the kit comprising a first primer and a second primer, wherein the first primer comprises a sequence substantially complementary to a portion of said template sequence and the second primer comprises a sequence substantially complementary to a portion of the complement of said template sequence, wherein the sequences within said primers define the termini of the template sequence to be amplified.

By "substantially complementary" in reference to a primer sequence it is meant that the primers have sufficient complementary to the template sequence, or complement thereof, to anneal to the template sequence, or complement thereof, at a temperature 45 to 65° C., e.g. 45, 46, 47, 48, 49, 50, 51, 52, 53, 54, 55, 56, 57, 58, 59, 60, 61, 62, 63, 64 or 65° C., at a salt concentration of 50 mM monovalent cations.

The template sequence (including the portions complementary to the primers) may be 50 nucleotides to 1500 nucleotides in length. For example, the template sequence may be 50, 75, 100, 150, 200, 250, 300, 400, 500, 600, 700, 800, 900, 1000, 1250 or 1500 nucleotides in length. In one embodiment, the template nucleic acid is contained within the nucleic acid sequence as recited in SEQ ID NO: 1 or SEQ ID NO: 2. In one embodiment, the template nucleic acid is the nucleic acid sequence as recited in SEQ ID NO: 1 or SEQ ID NO: 2. The primers of the invention are also suitable for use in detecting template sequences which differ from SEQ ID NO: 1 or SEQ ID NO: 2.

The invention also provides kits which further comprise a probe sequence substantially complementary to a portion of said template sequence or substantially complementary to a portion of the reverse complement of said template sequence. The probe sequence may also comprise a detectable label. By "substantially complementary" in reference to a probe sequence it is meant that the probes have sufficient complementary to the template sequence, or complement thereof, to anneal to the template sequence, or complement thereof, at a temperature 45 to 65° C., e.g. 45, 46, 47, 48, 49, 50, 51, 52, 53, 54, 55, 56, 57, 58, 59, 60, 61, 62, 63, 64 or 65° C., at a salt concentration of 50 mM monovalent cations.

The primers and probes may be 15, 16, 17, 18, 19, 20, 21, 22, 23, 24, 25, 30, 35, 40, 50 or more nucleotides in length. The probes and primers may comprise further nucleotides or other modifications at either the 5' end, the 3' end or both. The further nucleotides may comprise promoter sequences, restriction endonuclease recognition sites, or other nucleic acid sequences. In general, the probes and primers are not more than 100 nucleotides in length e.g. ≤75 nucleotides.

The primers and probes may also comprise one or more mis-matched nucleotides, for example for introducing site-specific mutations into the template sequence.

One particular primer pair which can be used in the kits and methods of the invention comprises the sequence of ARVD forward (GCRACAACTGARACAACWG-SEQ ID NO: 24) and ARVD reverse (GGAAGCAGTTGTCATCAAC-SEQ ID NO: 25). This primer pair may be used with any probe sequence, but in particular with a probe sequence comprising 6FAM-TTGCATATTAGATTGTCTCGCTGGTGTATA-Dabcyl (SEQ ID NO: 26) in qRT-PCR.

Further primer sequences are given in the table 2 below. In one embodiment, the primers are used in the following pairs: SEQ ID NOs: 27 & 28; SEQ ID NOs: 29 & 30; SEQ ID NOs: 31 & 32; SEQ ID NOs: 33 & 34; SEQ ID NOs: 35 & 36.

The invention also provides a method for diagnosing ARVD infection or to identify the presence or absence of an ARVD virus in a biological sample comprising the step of detecting the presence or absence of a nucleic acid molecule of the invention. In a particular embodiment, the methods involves the detection of the presence or absence of a nucleic acid comprising a nucleic acid sequence as recited in SEQ ID NO: 1 and/or SEQ ID NO: 2.

The detection step may be preceded by an amplification step, for example using any nucleic acid amplification techniques known in the art, and in particular LCR, PCR, RT-PCR, real-time PCR, real-time RT-PCR, qPCR, and qRT-PCR. Any suitable method may be used to detect the presence or absence of the nucleic acid of the invention, including but not limited to Southern blotting, northern blotting and agarose or polyacrylamide gel electrophoresis followed by visualisation of nucleic acids using ethidum bromide. The nucleic acid of the invention may also be detected using a real time assay (e.g. "qPCR"; Taqman™, Lightcycler™; Scorpion™ etc.).

Because ARVD has a RNA genome, in one particular embodiment of the invention, RT-PCR is used for the amplification step. However, equivalent RNA amplification methods are also applicable, as known to the person skilled in the art (NASBA™; 3SR™; TMAT™ etc). In a particular embodiment, a one step RT-real time PCR assay is applied ("one step RT-qPCR"). Commercially available RT-PCR kits may be used, e.g. Qiagen QuantiTect™ Virus kit or Invitrogen Super Script™ III Platinum™ kit. The generated fluorescence signals can be analyzed using the respective real time cycler software, as known in the art. The kits of the invention may therefore include reverse transcriptase.

Primers and probes as described above may be used in any of the methods of the invention.

The methods of the invention described above for the detection of the presence or absence of ARVD in a biological sample are particularly useful in screening poultry flocks, and in particular chicken flocks, for infection by ARVD. Screening of poultry for the presence or absence of ARVD can be used in methods to control or prevent outbreaks of RSS and MAS.

The methods of the invention described above are useful for screening poultry eggs for the presence or absence of ARVD. Screening eggs for the presence or absence of ARVD can be used to ensure that eggs used in vaccine production are ARVD-free.

The invention also provides a method for verifying that an egg is free from ARVD comprising detecting the presence or absence or ARVD in an egg. Any of the methods described above to detect the presence or absence of a nucleic acid of the invention can be used to verify than an egg is ARVD-free.

In the methods described above, the egg may be a chicken egg. In a further embodiment, the egg is an embyonated chicken egg and in particular an embryonated chicken egg for use in vaccine production. The vaccine being produced may be an influenza vaccine.

Antibodies and Immunoassays

In one embodiment, the invention provides antibodies that bind specifically to the polypeptides of the invention. In particular, an antibody of the invention binds specifically to a polypeptide consisting of the amino acid sequence of SEQ ID NO: 3 and/or SEQ ID NO: 4. By "binds specifically", it is meant that the antibodies bind to a polypeptide of the invention with substantially greater affinity than BSA. Preferably, the affinity is at least 100-fold, $10^3$-fold, $10^4$-fold, $10^5$-fold, $10^6$-fold etc. greater for the polypeptides of the invention than for BSA.

In one embodiment, the antibodies bind to the polypeptides of the invention with at least a 10-fold, 100-fold, $10^3$-fold, $10^4$-fold, $10^5$-fold, $10^6$-fold etc. greater affinity than its binding affinity to a VP6 polypeptide derived from any other Reovirus. In another embodiment, the antibody binds to a polypeptide of the invention with at least a 10-fold, 100-fold, $10^3$-fold, $10^4$-fold, $10^5$-fold, $10^6$-fold etc. greater affinity than its binding affinity to a VP6 polypeptide from another rotavirus.

The polypeptides of the invention which bind specifically to the antibodies of the invention are referred to as antigens.

"Antibody" as known in the art includes one or more biological moieties that, through chemical or physical means, can bind to an epitope of a polypeptide of interest. The antibodies of the invention include antibodies which specifically bind to an ARVD viral antigen from the VP6 polypeptides of the invention. The term "antibody" includes antibodies obtained from both polyclonal and monoclonal preparations, as well as the following: hybrid (chimeric) antibody molecules [38 and 39]; F(ab')2 and F(ab) fragments; Fv molecules [40 and 41]; single-chain Fv molecules (sFv) [42]; dimeric and trimeric antibody fragment constructs; and, any functional fragments obtained from such molecules, wherein such fragments retain immunological binding properties of the parent antibody molecule. The term "antibody" further includes antibodies obtained through non-conventional processes, such as phage display.

As used herein, the term "monoclonal antibody" refers to an antibody composition having a homogeneous antibody population. The term is not limited regarding the species or source of the antibody, nor is it intended to be limited by the manner in which it is made.

Antibodies are produced using techniques well known to those of skill in the art and disclosed in, for example references 43 and 44. For example, polyclonal antibodies are generated by immunizing a suitable animal, such as a mouse, rat, rabbit, sheep, chicken or goat, with an antigen of interest. In order to enhance immunogenicity, the antigen can be linked to a carrier prior to immunization. Such carriers are well known to those of ordinary skill in the art. Immunization is generally performed by mixing or emulsifying the antigen in saline, preferably in an adjuvant such as Freund's complete adjuvant, and injecting the mixture or emulsion parenterally (generally subcutaneously or intramuscularly). The animal is generally boosted 2-6 weeks later with one or more injections of the antigen in saline, preferably using Freund's incomplete adjuvant. Antibodies may also be generated by in vitro immunization, using methods known in the art. Polyclonal antiserum is then obtained from the immunized animal.

Monoclonal antibodies are generally prepared using the method of Kohler & Milstein [45], or a modification thereof. Typically, a mouse or rat is immunized as described above. Rabbits may also be used. However, rather than bleeding the animal to extract serum, the spleen (and optionally several large lymph nodes) is removed and dissociated into single cells. If desired, the spleen cells may be screened (after removal of non specifically adherent cells) by applying a cell suspension to a plate or well coated with the antigen. B-cells, expressing membrane-bound immunoglobulin specific for the antigen, will bind to the plate, and are not rinsed away with the rest of the suspension. Resulting B-cells, or all dissociated spleen cells, are then induced to fuse with myeloma cells to form hybridomas, and are cultured in a selective medium (e.g., hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected monoclonal antibody-secreting hybridomas are then cultured either in vitro (e.g., in tissue culture bottles or hollow fiber reactors), or in vivo (e.g., as ascites in mice).

The invention also provides kits and methods for the detection of the polypeptides of the invention. Any method known in the art for detecting polypeptides can be used. Such methods include, but are not limited to mass-spectrometry, immunodiffusion, immunoelectrophoresis, immunochemical methods, binder-ligand assays, immunohistochemical techniques, agglutination and complement assays [46].

The invention also provides methods for determining the presence or absence of ARVD in a biological sample by detecting the presence or absence of ARVD VP6 antigens or anti-ARVD VP6 antibodies in a biological sample comprising detecting the interaction of an anti-ARVD VP6 antibody, either a native antibody or an antibody of the invention, with an ARVD VP6 antigen.

A "native antibody" is an antibody present in a biological sample obtained from a subject, wherein the subject has been exposed to and mounted an immune response to ARVD VP6, resulting in the production of anti-ARVD VP6 antibodies. The subject may be mammalian or avian. In one embodiment, the subject is a chicken. In another embodiment, the subject is an embryonated egg.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin, and enzyme-labeled and mediated immunoassays, such as ELISA assays.

The immunoassay may be, without limitation, in a heterogeneous or in a homogeneous format, and of a standard or competitive type. In a heterogeneous format, the polypeptide is typically bound to a solid matrix or support to facilitate separation of the sample from the polypeptide after incubation. Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride, diazotized paper, nylon membranes, microchips, high or low density biochips, recombinant immunoassays (RIBA), microfluidity devices, micromagnetic beads, activated beads, and Protein A beads. For example, Dynatech Immunlon or Immunlon 2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies. Both standard and competitive formats are known in the art.

In a homogenous format, the test sample is incubated with the combination of antigens in solution. For example, it may be under conditions that will precipitate any antigen-antibody complexes which are formed. Both standard and competitive formats for these assays are known in the art.

In a standard format, the amount of anti-ARVD VP6 antibodies in the antibody-antigen complexes is detected. This may be accomplished by determining whether labeled anti-xenogeneic (e.g., anti-chicken) antibodies which recognize an epitope on anti-ARVD VP6 antibodies will bind due to complex formation. In a competitive format, the amount of anti-ARVD VP6 antibodies in the sample is deduced by monitoring the competitive effect on the binding of a known amount of labeled antibody (or other competing ligand) in the complex.

Complexes formed comprising anti-ARVD VP6 antibody (or in the case of competitive assays, the amount of competing antibody) are detected by any of a number of known techniques, depending on the format. For example, unlabeled anti-ARVD VP6 antibodies in the complex may be detected using a conjugate of antixenogeneic Ig complexed with a label, (e.g., an enzyme label).

In an immunoprecipitation or agglutination assay format the reaction between the ARVD antigens and the antibody forms a network that precipitates from the solution or suspension and forms a visible layer or film of precipitate. If no anti-ARVD VP6 antibody is present in the test specimen, no visible precipitate is formed.

There are at least three specific types of particle agglutination (PA) assays. These assays are used for the detection of antibodies to various antigens when coated to a support. One type of this assay is the hemagglutination assay using red blood cells (RBCs) that are sensitized by passively adsorbing antigen (or antibody) to the RBC. The addition of specific antigen antibodies present in the body component, if any, causes the RBCs coated with the purified antigen to agglutinate.

To eliminate potential non-specific reactions in the hemagglutination assay, two artificial carriers may be used instead of RBC in the PA. The most common of these are latex particles. However, gelatin particles may also be used. The assays utilizing either of these carriers are based on passive agglutination of the particles coated with purified antigens.

The anti-ARVD VP6 antigens will typically be packaged in the form of a kit for use in these immunoassays. The kit will normally contain in separate containers the ARVD VP6 antigen, control antibody formulations (positive and/or negative), labeled antibody when the assay format requires same and signal generating reagents (e.g., enzyme substrate) if the label does not generate a signal directly. The ARVD VP6 antigen may be already bound to a solid matrix or separate with reagents for binding it to the matrix. Instructions (e.g., written, CD-ROM, etc.) for carrying out the assay usually will be included in the kit.

In an alternative embodiment of the invention the presence or absence of ARVD in a biological sample may be determined by means of immunohistochemistry (the use of antibodies to probe specific antigens in a sample). Said analysis is standard in the art, wherein detection of antigens in tissues is known as immunohistochemistry, while detection in cultured cells is generally termed immunocytochemistry. Briefly the primary antibody to be detected by binding to its specific antigen. The antibody-antigen complex is then bound by a secondary enzyme conjugated antibody. In the presence of the necessary substrate and chromogen the bound enzyme is detected according to coloured deposits at the antibody-antigen binding sites. There is a wide range of suitable sample types, antigen-antibody affinity, antibody types, and detection enhancement methods. Thus optimal conditions for immunohistochemical or immunocytochemical detection must be determined by the person skilled in the art for each individual case.

Immunoassays, immunohistochemical detection and immunocytochemical detection methods of the invention for the presence or absence of ARVD in a biological sample are particularly useful in screening poultry flocks, and in particular chicken flocks, for infection by ARVD. Screening of poultry for the presence of ARVD can be used in methods to control or prevent outbreaks of RSS and MAS.

Immunoassays, immunohistochemical detection and immunocytochemical detection methods of the invention are also useful for screening poultry eggs for the presence or absence of ARVD. Screening eggs for the presence or absence of ARVD can be used to ensure that eggs used in vaccine production are ARVD-free.

The invention also provides a method for verifying that an egg is free from ARVD comprising detecting the presence or absence or ARVD in an egg. Any of the methods described above to detect the presence or absence of a polypeptide of the invention or an anti-ARVD antibody can be used to verify than an egg is ARVD-free.

In the methods described above, the egg may be a chicken egg. In a further embodiment, the egg is an embyonated chicken egg and in particular an embryonated chicken egg for use in vaccine production. The vaccine being produced may be an influenza vaccine.

Antibodies of the invention are preferably provided in purified or substantially purified form. Typically, the antibody will be present in a composition that is substantially free of other polypeptides e.g. where less than 90% (by weight), usually less than 60% and more usually less than 50% of the composition is made up of other polypeptides.

Vaccines

The invention also provides a vaccine for the treatment of or protection against infection by ARVD, and in one embodiment is used for the treatment or prevention of RSS and/or MAS. Vaccine formulations of the invention include an attenuated ARVD virus comprising a polypeptide of the invention or a recombinant or purified subunit formulation of one or more ARVD viral antigens including an ARVD VP6 antigen. The vaccine formulations may further comprise an adjuvant.

The invention includes a composition comprising an attenuated ARVD virus which has a VP6 polypeptide sequence as described herein. This composition can be used as a prophylactic or therapeutic ARVD virus vaccine. Methods of attenuating viruses are known in the art. Such methods include serial passage of the ARVD virus in cultured cells (e.g., avian or mammalian cell culture), until the ARVD virus demonstrates attenuated function. The temperature at which the virus is grown can be any temperature at which with tissue culture passage attenuation occurs. Attenuated function of the ARVD virus after one or more passages in cell culture can be measured by one skilled in the art. As used herein, attenuation refers to the decreased virulence of the ARVD virus in a poultry subject, in particular in a chicken. Evidence of attenuated function may be indicated by decreased levels of viral replication or by decreased virulence in an animal model.

In a specific embodiment, the ARVD is attenuated by introducing mutations into the nucleic acid sequence encoding the VP6 polypeptide.

Other methods of producing an attenuated ARVD virus include passage of the virus in cell culture at sub-optimal or "cold" temperatures and introduction of attenuating mutations into the ARVD viral genome by random mutagenesis (e.g., chemical mutagenesis) or site specific directed mutagenesis. Preparation and generation of attenuated RSV vaccines (the methods of which will generally applicable to ARVD virus) are disclosed in, for example references 47 to 50.

The invention includes a composition comprising an isolated or purified ARVD viral antigen derived from the polypeptides of the invention. In particular, the invention provides a vaccine composition comprising a polypeptide of the invention or an antigenic fragment thereof. The composition may further comprise one or more adjuvants.

ARVD viral antigens can be isolated or purified from an ARVD virus grown in cell culture. Alternatively, ARVD viral antigens can be recombinantly produced by methods known in the art.

The ARVD viral antigens used in the invention can be produced in a variety of different expression systems which are known in the art; for example those used with mammalian cells, baculoviruses, bacteria, and yeast. Such expression systems will typically use polynucleotides encoding the viral antigens of the invention. Such sequences can be obtained using standard techniques of molecular biology, including translating the amino acid sequences listed herein. Accordingly, the invention includes polynucleotides encoding for the viral antigens of the invention. In addition, the viral antigens of the invention can be produced (at least in part, preferably in whole) via synthetic chemistry methods.

The vaccines of the invention may be administered by any route know in the art for the administration of vaccines, including intramuscular or subcutaneous injection, intra-ocular administration, intranasal administration or oral administration. In one embodiment, the ABVD vaccine of the invention is suitable for oral administration. In particular, the vaccine may be administered to poultry flocks using drinking water.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

References to a percentage sequence identity between two sequences means that, when aligned, that percentage of monomers are the same in comparing the two sequences. This alignment and the percent homology or sequence identity can be determined using software programs known in the art, for example those described in section 7.7.18 of reference 51. Identity between amino acid or nucleotide sequences is preferably determined by the Smith-Waterman homology search algorithm [52], using an affine gap search with default parameters gap open penalty=12 and gap extension penalty=1. The BLOSUM62 scoring matrix can be used.

As indicated in the above text, nucleic acids and polypeptides of the invention may include sequences that:

(a) are identical (i.e. 100% identical) to a sequence from SEQ ID NOs: 1 to 4;
(b) share sequence identity with a sequence from SEQ ID NOs: 1 to 4;
(c) have 1, 2, 3, 4, 5, 6, 7, 8, 9 or 10 single nucleotide or amino acid alterations (deletions, insertions, substitutions), which may be at separate locations or may be contiguous, as compared to the sequences of (a) or (b); and
(d) when aligned with a particular sequence from SEQ ID NOs 1 to 4 using a pairwise alignment algorithm, a moving window of x monomers (amino acids or nucleotides) moving from start (N-terminus or 5') to end (C-terminus of 3'), such that for an alignment that extends to p monomers (where p>x) there are p−x+1 such windows, each window has at least xy identical aligned monomers, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [53], using default parameters (e.g. with Gap opening penalty=10.0, and with Gap extension penalty=0.5, using the EBLOSUM62 scoring matrix). This algorithm is conveniently implemented in the needle tool in the EMBOSS package [54].

The nucleic acids and polypeptides of the invention may additionally have further sequences to the N-terminus/5' and/or C-terminus/3' of these sequences (a) to (d).

The practice of the present invention will employ, unless otherwise indicated, conventional methods of chemistry, biochemistry, molecular biology, immunology and pharmacology, within the skill of the art. Such techniques are explained fully in the literature. See, e.g., references 55-62, etc.

BRIEF DESCRIPTION OF THE DRAWINGS

FIG. 1: Amplification plots of an ARVD positive sample in serial dilutions (2 fold) and negative control (water).

FIG. 2: ClustalW alignment of SEQ ID NO: 1 and SEQ ID NO: 2

FIG. 3: ClustalW alignment of SEQ ID NO: 3 and SEQ ID NO: 4

MODES FOR CARRYING OUT THE INVENTION

Materials and Methods

Intestinal-content Sample

Intestinal content was collected from a stunted chick at a age of 10 days. Numerous particles of ARVD were identified by PAGE in this intestinal content of the chick. The preparation of the sample, the isolation of viral ds RNA and the PAGE were described in reference 6.

Qiagen QIAamp Viral RNA Mini Kit, Gel Extraction of VP6Genome Segment

Amplification and Cloning of Viral dsRNA (Modified Method Described by in Reference 63)

Oligo ligation: 10 μl dsRNA, 2.5 μl primer PC3 100 μM, 1 μl RNAse Inhibitor, 2.5 μl BSA, 2.5 μl ATP 10 mM, 4 μl RNA ligase, 2.75 μl buffer and 2.5 μl PEG 4000 were incubated for 24 h at 17° C. Ligated dsRNAs were diluted in TE buffer to 100 μl and purified over Eppendorf gel extraction column as described by the manufacturer. To the elute 1 μl oligoT17, 100 μM and 1.5 μl DMSO were added and incubated at 99° C. in a thermocycler for 2 minutes and chilled on ice. Immediately after this step following reagents were added: 2 μl water, 1 μl Ribolock, 1.5 μl TRIS pH8.3 1M, 6 μl MgCL2 50 mM, 2.1 μl KCl 1M, 6 μl dNTPs 2.5 mM, 0.35 μl AMV reverse transcriptase. The reaction was incubated at 42° C. for 45 minutes followed by incubation at 50° C. for 15 minutes. The reaction was stopped by the addition of 1 μl EDTA 1M. Residual RNA was removed by the addition of 3.4 μl NaOH 1M and incubation at 65° C. for 30 minutes.

The annealing of the cDNA's was performed for one hour at 65° C. after adding of 4.3 μl Tris (pH7.5, 1M) and 4.3 μl HCl (1M). 5 μl of the cDNA reaction was added to a 50 μl PCR reaction containing 5 μl Ex Taq buffer, 4 μl dNTPs 2.5 mM, 1 μl PC2 primer 100 μM, 1 μl Ex Taq. During the preincubation for 5 minutes at 72° C. the partial overhangs of the cDNA's are filled in. This is followed by a 2 minutes incubation of 94° C. and 30 cycles of 94° C. for 30 seconds, 67° C. for 30 seconds and 72° C. for 5 minutes. The quality and quantity of the PCR amplicons was checked by agarose gel electrophoresis. PCR products were cloned by T/A cloning and sequenced.

qRT-PCR

To 1-4 μl dsRNA (extracted with QIAGEN QIAamp viral RNA Mini kit) 3 μl of each 10 μM primer were added (ARVD forward GCRACAACTGARACAACWG (SEQ ID NO: 24))

and ARVD reverse GGAAGCAGTTGTCATCAAC (SEQ ID NO: 25)) and denatured at 99° C. for 10 minutes. PCR tubes were chilled on ice and the mastermix (10 µl Eppendorf RealMasterMix RT probe 2.5×, 0.5 µl ARDV 10 µM probe (6FAM-TTGCATATTAGATTGTCTCGCTGGTGTATA-Dabcyl (SEQ ID NO: 26)), 0.25 µl realMaster RT Enzyme, 0.25 µl RNase Inhibitor solution) and PCR grade water up to a total of 25 µl were added. Reverse transcription was performed at 50° C. for 30 minutes, followed by an initial denaturation at 95° C. for 2 minutes and 45 two-step cycles of 10 seconds denaturation at 95° C. and annealing/amplification for 30 seconds at 60° C. on a Stratagene Mx3000P realtime PCR machine.

Results

The results of the qRT-PCR are shown in FIG. 1. The sequence of the amplified fragment is given in SEQ ID NO: 1

The complete ARVD VP6 nucleotide sequence is given in SEQ ID NO: 2. The encoded polypeptide sequence is given in SEQ ID NO: 4.

It will be understood that the invention has been described by way of example only and modifications may be made whilst remaining within the scope and spirit of the invention.

TABLE 1

PREDICTED EPITOPES

| SEQ ID No. | Start Position | End Position | Amino acid sequence | Peptide Length |
|---|---|---|---|---|
| 5 | 4 | 12 | LSSIALTVR | 9 |
| 6 | 24 | 33 | YSNVSDVIQQ | 10 |
| 7 | 37 | 43 | MVRVLNG | 7 |
| 8 | 62 | 78 | DLPQLGTTLLNIDANYV | 17 |
| 9 | 88 | 103 | LTEFVIAVCETELLVD | 16 |
| 10 | 111 | 119 | PQSEALRLL | 9 |
| 11 | 121 | 128 | NNKYVFLN | 8 |
| 12 | 137 | 144 | EWHYRLSA | 8 |
| 13 | 150 | 162 | SNHVPYIFPYDMA | 13 |
| 14 | 164 | 174 | AYDRVTAAYDN | 11 |
| 15 | 183 | 195 | LNNAIHFAAFDQD | 13 |
| 16 | 207 | 235 | FEYLYNLRTPVSNATIVIHPISILSVPSM | 29 |
| 17 | 241 | 247 | ATHYWPY | 7 |
| 18 | 260 | 275 | RVEFQLAGQVIYVAAN | 16 |
| 19 | 281 | 290 | IPQFDAVNII | 10 |
| 20 | 292 | 306 | TMRRLPLLADLQNIF | 15 |
| 21 | 314 | 328 | THQAVISTKIEVLNA | 15 |
| 22 | 333 | 347 | TVPSIDEHLYALIVG | 15 |
| 23 | 355 | 362 | QAGPVFPP | 8 |

TABLE 2

PRIMER SEQUENCES

| SEQ ID NO: | Forward | SEQ ID NO: | Reverse |
|---|---|---|---|
| 27 | TTAGAAACCAAGCTGCCACA | 28 | TGCAAATCAGCTAGCAATGG |
| 29 | TGCCATTGCTAGCTGATTTG | 30 | ACGCATACCAGGAGGAAAGA |
| 31 | AACCAAGCTGCCACACACTA | 32 | TGCAAATCAGCTAGCAATGG |
| 33 | AAACCAAGCTGCCACACACT | 34 | AAACCAAGCTGCCACACACT |
| 35 | ATTTGAGGACGCCAGTGTCT | 36 | ATTTGAGGACGCCAGTGTCT |

References

1 Pesavento J B, Crawford S E, Estes M K, Prasad B V (2006). Curr. Top. Microbiol. Immunol. 309:189-219
2 Bishop R F (1996). Arch. Virol. Suppl. 12: 119-28
3 Songserm T, Pol J M, van Roozelaar D, Kok G L, Wagenaar F, ter Huurne A A. (2000) Avian Dis. 44(3):556-67
4 Page R K, Fletcher O J, Rowland G N, Gaudry D, Villegas P. (1982) Avian Dis. 26(3):618-24
5 Bellinzoni R, Manion N, Vallejos L, La Torre J L, Scodeller E A. (1987) Res Vet Sci. 43(1):130-1
6 Otto P, Liebler-Tenorio E M, Elschner M, Reetz J, Löhren U, Diller R. (2006) Avian Dis. 50(3):411-8
7 M. S. McNulty, G. M. Allan, D. Todd, J. B. McFerran and R. M. McCracken (1981). J Gen Virol. 55:405-413
8 Boards, G. M. et al. Journal of Clinical Microbiology, 19: 248-254 (1984).
9 Trojnar E, Otto P, Roth B, Reetz J and Johne R. (2010) 1 Virol 84(19): 10254-10265.
10 Kricka, Nonisotopic DNA Probe Techniques, 1992, Academic Press San Diego, Calif.
11 U.S. Pat. No. 5,514,758,
12 U.S. Pat. No. 5,565,552
13 U.S. Pat. No. 5,567,810
14 U.S. Pat. No. 5,574,142
15 U.S. Pat. No. 5,585,481
16 U.S. Pat. No. 5,587,371
17 U.S. Pat. No. 5,597,696
18 U.S. Pat. No. 5,958,773
19 Geysen et al. (1984) *PNAS USA* 81:3998-4002.
20 Carter (1994) *Methods Mol Biol* 36:207-23.
21 Jameson, BA et al. 1988, *CABIOS* 4(1):181-186.
22 Raddrizzani & Hammer (2000) *Brief Bioinform* 1(2):179-89.
23 De Lalla et al. (1999) *J. Immunol.* 163:1725-29.
24 Brusic et al. (1998) *Bioinformatics* 14(2):121-30
25 Meister et al. (1995) *Vaccine* 13(6):581-91.
26 Roberts et al. (1996) *AIDS Res Hum Retroviruses* 12(7): 593-610.
27 Maksyutov & Zagrebelnaya (1993) *Comput Appl Biosci* 9(3):291-7.
28 Feller & de la Cruz (1991) *Nature* 349(6311):720-1.
29 Hopp (1993) *Peptide Research* 6:183-190.
30 Welling et al (1985) *FEBS Lett.* 188:215-218.
31 Davenport et al. (1995) *Immunogenetics* 42:392-297.
32 Kolaskar A S, Tongaonkar P C. (1990) Dec. 10; 276(1-2): 172-4.
33 Bodanszky (1993) *Principles of Peptide Synthesis* (ISBN: 0387564314).
34 Fields et al. (1997) *Meth Enzymol* 289: *Solid-Phase Peptide Synthesis.* ISBN: 0121821900.
35 Chan & White (2000) *Fmoc Solid Phase Peptide Synthesis.* ISBN: 0199637245.
36 Kullmann (1987) *Enzymatic Peptide Synthesis.* ISBN: 0849368413.
37 Ibba (1996) *Biotechnol Genet Eng Rev* 13:197-216.
38 Winter et al. (1991) *Nature* 349: 293-299
39 U.S. Pat. No. 4,816,567
40 Inbar et al. (1972) Proc Natl Acad Sci USA 69:2659-2662
41 Ehrlich et al. (1980) Biochem 19:4091-4096
42 Huston et al. (1988) Proc Natl Acad Sci USA 85:5897-5883
43 U.S. Pat. No. 4,011,308
44 U.S. Pat. No. 4,722,890
45 Kohler & Milstein (1975) Nature 256:495-497
46 Basic and Clinical Immunology, Sites and Terr, eds., Appleton & Lange, Norwalk, Conn. pp 217-262, 1991
47 EP 0 640 128
48 U.S. Pat. No. 6,284,254
49 U.S. Pat. No. 5,922,326
50 U.S. Pat. No. 5,882,651
51 *Current Protocols in Molecular Biology* (F. M. Ausubel et al., eds., 1987) Supplement 30
52 Smith and Waterman, Adv. Appl. Math. (1981) 2: 482-489.
53 Needleman & Wunsch (1970) *J. Mol. Biol.* 48, 443-453.
54 Rice et al. (2000) Trends Genet 16:276-277.
55 Gennaro (2000) *Remington: The Science and Practice of Pharmacy.* 20th edition, ISBN: 0683306472.
56 *Methods In Enzymology* (S. Colowick and N. Kaplan, eds., Academic Press, Inc.)
57 *Handbook of Experimental Immunology*, Vols. I-IV (D. M. Weir and C. C. Blackwell, eds., 1986, Blackwell Scientific Publications)
58 Sambrook, et al., *Molecular Cloning: A Laboratory Manual* (2nd Edition, 1989).
59 *Handbook of Surface and Colloidal Chemistry* (Birdi, K. S. ed., CRC Press, 1997)
60 *Short Protocols in Molecular Biology,* 4th ed. (Ausubel et al. eds., 1999, John Wiley & Sons)
61 *Molecular Biology Techniques: An Intensive Laboratory Course,* (Ream et al., eds., 1998, Academic Press)
62 PCR (*Introduction to Biotechniques Series*), 2nd ed. (Newton & Graham eds., 1997, Springer Verlag)
63 Potgieter A C, Steele A D and van Dijk A A (2002). J Gen. Virol. 83, 2215-2223

The invention claimed is:

1. A nucleic acid comprising:
    (a) a nucleic acid sequence with at least 90% identity to the nucleic acid sequence as recited in SEQ ID NO: 1;
    (b) a nucleic acid sequence with at least 90% identity to the reverse complement of the nucleic acid sequence as recited in SEQ ID NO: 1;
    (c) a fragment of the nucleic acid sequence as recited in SEQ ID NO: 1 that consists of at least 24 consecutive nucleotides from SEQ ID NO: 1;
    (d) a fragment of the reverse complement of the nucleic acid sequence as recited in SEQ ID NO: 1 that consists of at least 10 consecutive nucleotides of the reverse complement SEQ ID NO: 1; or
    (e) a nucleic acid sequence which hybridizes under high stringency conditions with a nucleic acid sequence as recited in SEQ ID NO: 1, wherein the nucleic acid comprises a detectable label selected from a radioisotope, a chromophore, a fluorescent molecule, a quencher molecule, a biotin molecule, or a hairpin structure.

2. The nucleic acid of claim 1, wherein the detectable label comprises the fluorescent molecule.

3. A kit comprising primers for amplifying a template sequence contained within a ARVD virus nucleic acid, the kit comprising a first primer and a second primer, wherein the first primer comprises a sequence of at least 10 nucleotides substantially complementary to a portion of said template sequence and the second primer comprises a sequence of at least 10 nucleotides substantially complementary to a portion of the complement of said template sequence; wherein the sequences within said primers which have substantial complementarity define the termini of the template sequence to be amplified; wherein the first primer is 100 nucleotides or less and the second primer is 100 nucleotides or less; wherein the first primer or the second primer comprises a detectable label selected from a radioisotope, a chromophore, a fluorescent molecule, a quencher molecule, a biotin molecule, or a hairpin structure or the kit further comprises a probe sequence comprising the detectable label substantially complementary to a portion of said template sequence or substantially complementary to a portion of the reverse complement of said template sequence; and wherein the ARVD virus nucleic acid sequence is:
    (a) a nucleic acid sequence with at least 90% identity to the nucleic acid sequence as recited in SEQ ID NO: 1;
    (b) a nucleic acid sequence with at least 90% identity to the reverse complement of the nucleic acid sequence as recited in SEQ ID NO: 1;
    (c) a fragment of the nucleic acid sequence as recited in SEQ ID NO: 1 that consists of at least 24 consecutive nucleotides from SEQ ID NO: 1;
    (d) a fragment of the reverse complement of the nucleic acid sequence as recited in SEQ ID NO: 1 that consists of at least 10 consecutive nucleotides of the reverse complement SEQ ID NO: 1; or
    (e) a nucleic acid sequence which hybridizes under high stringency conditions with a nucleic acid sequence as recited in SEQ ID NO: 1.

4. The kit of claim 3, further comprising a probe sequence substantially complementary to a portion of said template sequence or substantially complementary to a portion of the reverse complement of said template sequence.

5. The kit of claim 3, wherein the template sequence is contained within a nucleic acid sequence as recited in SEQ ID NO: 1.

6. A method for diagnosing ARVD infection or to identify the presence or absence of an ARVD virus in a biological sample, comprising the steps of contacting the biological sample with the nucleic acid molecule of claim 1 and detecting the presence or absence of the ARVD virus.

7. A polypeptide comprising:
    (a) an amino acid sequence with at least 90% identity to the amino acid sequence encoded by SEQ ID NO: 1; or
    (b) a fragment of the amino acid sequence encoded by SEQ ID NO: 1 that consists of at least 9 consecutive amino acids encoded by SEQ ID NO: 1, wherein the polypeptide comprises a detectable label selected from an enzymatic molecule, a fluorescent molecule, a chemiluminescent molecule, a radioactive molecule, a dye molecule, a biotin molecule, or an avidin molecule.

8. An antibody that specifically binds to a polypeptide comprising:
    (a) an amino acid sequence with at least 90% identity to the amino acid sequence encoded by SEQ ID NO: 1; or
    (b) a fragment of the amino acid sequence encoded by SEQ ID NO: 1 that consists of at least 9 consecutive amino acids encoded by SEQ ID NO: 1 and/or antigenic fragments thereof, wherein the antibody is selected from the group consisting of (i) a non-avian antibody, (ii) a labeled antibody, and (iii) a monoclonal antibody population.

9. The antibody of claim 8, wherein the antibody is the monoclonal antibody population.

10. An immunoassay for detecting the presence or absence of an ARVD antigen in a biological sample, comprising the step of contacting the sample with the antibody of claim 8.

11. The method of claim 6, wherein the biological sample is an egg.

12. A vaccine for the treatment of or protection against ARVD comprising an immunostimulatory amount of an adjuvant and a polypeptide comprising:
    (a) an amino acid sequence with at least 90% identity to the amino acid sequence encoded by SEQ ID NO: 1; or
    (b) a fragment of the amino acid sequence encoded by SEQ ID NO: 1 that consists of at least 9 consecutive amino acids encoded by SEQ ID NO: 1.

* * * * *

SEQUENCE LISTING

<160> NUMBER OF SEQ ID NOS: 36

<210> SEQ ID NO 1
<211> LENGTH: 363
<212> TYPE: DNA
<213> ORGANISM: Avian rotavirus D

<400> SEQUENCE: 1

| | | | | | | |
|---|---|---|---|---|---|---|
| gcgacaactg | agacaactgt | gccatctatt | aatgaacatt | tgtatgcttt | aattgtagga | 60 |
| actagaggta | gatatcagat | gcaggctgga | ccagtctttc | ctcctggtat | gcgttgggat | 120 |
| gatattctga | ataggtatac | accagcgaga | caatctaata | tgcaacggtt | gatgacaact | 180 |
| gcttccatac | ttgatctagt | ttccatgtag | gcgcggaaga | tgccactcga | gataacatca | 240 |
| aggttaaaat | acgtggaact | aggctgagta | tgtggcacag | taatgcggag | taatatctgc | 300 |
| atggaagaaa | tctgttatca | tacgtcagca | gctattatct | ttgaccggat | cccgggaatt | 360 |
| cgg | | | | | | 363 |

<210> SEQ ID NO 2
<211> LENGTH: 1194
<212> TYPE: DNA
<213> ORGANISM: Avian Rotavirus D
<220> FEATURE:
<221> NAME/KEY: misc_feature
<222> LOCATION: 408
<223> OTHER INFORMATION: n is any nucleotide
<220> FEATURE:
<221> NAME/KEY: misc_feature
<222> LOCATION: 690
<223> OTHER INFORMATION: n is any nucleotide

<400> SEQUENCE: 2

| | | | | | | |
|---|---|---|---|---|---|---|
| atggaggcgc | tgtcttcaat | tgcgttgact | gtcagagaag | cacgagaaaa | gatcataaat | 60 |
| ggaacaatat | attccaacgt | gtcggatgta | atacaacaat | tcaatcaaat | ggttagagta | 120 |
| ttgaatggat | caacttttac | tactggtgga | ttggctacta | tgccacttag | agaatggact | 180 |
| tttgatctgc | cgcaattggg | tacaacttta | ctaaatatag | atgctaatta | tgtagaatca | 240 |
| atgacaccaa | cacttgatat | gttgactgag | tttgtgattg | ctgtatgtga | aactgagttg | 300 |
| ctagttgata | caatagaaa | tggtgcatac | ccacaatctg | aagcattgag | attactatct | 360 |
| aacaataaat | atgttttcct | taatatggat | ttaggatcta | agtacatntc | agaatggcat | 420 |
| tatagattgt | cagctaggga | tccaatgttt | tcaaatcatg | taccatatat | attcccatat | 480 |
| gatatggcta | tagcatatga | tagagtaacg | gctgcttacg | ataatgtgtc | aggaacacga | 540 |
| tttgcatcac | taaataatgc | tatacatttt | gctgcatttg | atcaagactt | tgttcgtgga | 600 |
| cagccagcta | atgcgaggca | atttgaatac | ctttacaatt | tgaggacgcc | agtgtctaat | 660 |
| gctactatag | tcatacatcc | aatatcagan | attttgtcag | taccaagtat | gattagaaac | 720 |
| caagctgcca | cacactattg | gccatacaac | ccatataata | taccgacgtt | tagagatgac | 780 |
| attagagttg | aattccaact | tgcaggacaa | gtaatatatg | tagctgcgaa | tctgggaatg | 840 |
| catactattc | cgcaatttga | tgcagtaaat | atcatcttga | caatgaggag | attgccattg | 900 |
| ctagctgatt | tgcaaaatat | attcccagct | ggaaatccat | cagcaacaca | tcaagctgta | 960 |
| atttcaacta | aaattgaagt | gctgaatgcg | acaactgaaa | caactgtacc | atctattgat | 1020 |
| gaacatttgt | atgctttaat | tgtaggaact | agaggtagat | atcagatgca | ggctggacca | 1080 |
| gtctttcctc | ctggtatgcg | ttgggatgat | attctgaata | ggtatacacc | agcaagacaa | 1140 |
| tctaatatgc | aacggttgat | gacaactgct | tccatacttg | atctagtttc | catg | 1194 |

<210> SEQ ID NO 3
<211> LENGTH: 69
<212> TYPE: PRT
<213> ORGANISM: Avian Rotavirus D

<400> SEQUENCE: 3

Ala Thr Thr Glu Thr Thr Val Pro Ser Ile Asn Glu His Leu Tyr Ala
1 5 10 15

Leu Ile Val Gly Thr Arg Gly Arg Tyr Gln Met Gln Ala Gly Pro Val
20 25 30

Phe Pro Pro Gly Met Arg Trp Asp Asp Ile Leu Asn Arg Tyr Thr Pro
35 40 45

Ala Arg Gln Ser Asn Met Gln Arg Leu Met Thr Thr Ala Ser Ile Leu
50 55 60

Asp Leu Val Ser Met
65

<210> SEQ ID NO 4
<211> LENGTH: 398
<212> TYPE: PRT
<213> ORGANISM: Avian Rotavirus D
<220> FEATURE:
<221> NAME/KEY: misc_feature
<222> LOCATION: 136
<223> OTHER INFORMATION: Xaa is any amino acid
<220> FEATURE:
<221> NAME/KEY: misc_feature
<222> LOCATION: 230
<223> OTHER INFORMATION: Xaa is any amino acid

<400> SEQUENCE: 4

Met Glu Ala Leu Ser Ser Ile Ala Leu Thr Val Arg Glu Ala Arg Glu
1 5 10 15

Lys Ile Ile Asn Gly Thr Ile Tyr Ser Asn Val Ser Asp Val Ile Gln
20 25 30

Gln Phe Asn Gln Met Val Arg Val Leu Asn Gly Ser Thr Phe Thr Thr
35 40 45

Gly Gly Leu Ala Thr Met Pro Leu Arg Glu Trp Thr Phe Asp Leu Pro
50 55 60

Gln Leu Gly Thr Thr Leu Leu Asn Ile Asp Ala Asn Tyr Val Glu Ser
65 70 75 80

Met Thr Pro Thr Leu Asp Met Leu Thr Glu Phe Val Ile Ala Val Cys
85 90 95

Glu Thr Glu Leu Leu Val Asp Asn Asn Arg Asn Gly Ala Tyr Pro Gln
100 105 110

Ser Glu Ala Leu Arg Leu Leu Ser Asn Asn Lys Tyr Val Phe Leu Asn
115 120 125

Met Asp Leu Gly Ser Lys Tyr Xaa Ser Glu Trp His Tyr Arg Leu Ser
130 135 140

Ala Arg Asp Pro Met Phe Ser Asn His Val Pro Tyr Ile Phe Pro Tyr
145 150 155 160

Asp Met Ala Ile Ala Tyr Asp Arg Val Thr Ala Ala Tyr Asp Asn Val
165 170 175

Ser Gly Thr Arg Phe Ala Ser Leu Asn Asn Ala Ile His Phe Ala Ala
180 185 190

Phe Asp Gln Asp Phe Val Arg Gly Gln Pro Ala Asn Ala Arg Gln Phe
195 200 205

```
Glu Tyr Leu Tyr Asn Leu Arg Thr Pro Val Ser Asn Ala Thr Ile Val
    210                 215                 220

Ile His Pro Ile Ser Xaa Ile Leu Ser Val Pro Ser Met Ile Arg Asn
225                 230                 235                 240

Gln Ala Ala Thr His Tyr Trp Pro Tyr Asn Pro Tyr Asn Ile Pro Thr
                245                 250                 255

Phe Arg Asp Asp Ile Arg Val Glu Phe Gln Leu Ala Gly Gln Val Ile
                260                 265                 270

Tyr Val Ala Ala Asn Leu Gly Met His Thr Ile Pro Gln Phe Asp Ala
            275                 280                 285

Val Asn Ile Ile Leu Thr Met Arg Arg Leu Pro Leu Leu Ala Asp Leu
    290                 295                 300

Gln Asn Ile Phe Pro Ala Gly Asn Pro Ser Ala Thr His Gln Ala Val
305                 310                 315                 320

Ile Ser Thr Lys Ile Glu Val Leu Asn Ala Thr Thr Glu Thr Thr Val
                325                 330                 335

Pro Ser Ile Asp Glu His Leu Tyr Ala Leu Ile Val Gly Thr Arg Gly
                340                 345                 350

Arg Tyr Gln Met Gln Ala Gly Pro Val Phe Pro Gly Met Arg Trp
            355                 360                 365

Asp Asp Ile Leu Asn Arg Tyr Thr Pro Ala Arg Gln Ser Asn Met Gln
370                 375                 380

Arg Leu Met Thr Thr Ala Ser Ile Leu Asp Leu Val Ser Met
385                 390                 395

<210> SEQ ID NO 5
<211> LENGTH: 9
<212> TYPE: PRT
<213> ORGANISM: Avian Rotavirus D

<400> SEQUENCE: 5

Leu Ser Ser Ile Ala Leu Thr Val Arg
1               5

<210> SEQ ID NO 6
<211> LENGTH: 10
<212> TYPE: PRT
<213> ORGANISM: Avian Rotavirus D

<400> SEQUENCE: 6

Tyr Ser Asn Val Ser Asp Val Ile Gln Gln
1               5                   10

<210> SEQ ID NO 7
<211> LENGTH: 7
<212> TYPE: PRT
<213> ORGANISM: Avian Rotavirus D

<400> SEQUENCE: 7

Met Val Arg Val Leu Asn Gly
1               5

<210> SEQ ID NO 8
<211> LENGTH: 17
<212> TYPE: PRT
<213> ORGANISM: Avian Rotavirus D

<400> SEQUENCE: 8

Asp Leu Pro Gln Leu Gly Thr Thr Leu Leu Asn Ile Asp Ala Asn Tyr
1               5                   10                  15
```

Val

<210> SEQ ID NO 9
<211> LENGTH: 16
<212> TYPE: PRT
<213> ORGANISM: Avian Rotavirus D

<400> SEQUENCE: 9

Leu Thr Glu Phe Val Ile Ala Val Cys Glu Thr Glu Leu Leu Val Asp
1 5 10 15

<210> SEQ ID NO 10
<211> LENGTH: 9
<212> TYPE: PRT
<213> ORGANISM: Avian Rotavirus D

<400> SEQUENCE: 10

Pro Gln Ser Glu Ala Leu Arg Leu Leu
1 5

<210> SEQ ID NO 11
<211> LENGTH: 8
<212> TYPE: PRT
<213> ORGANISM: Avian Rotavirus D

<400> SEQUENCE: 11

Asn Asn Lys Tyr Val Phe Leu Asn
1 5

<210> SEQ ID NO 12
<211> LENGTH: 8
<212> TYPE: PRT
<213> ORGANISM: Avian Rotavirus D

<400> SEQUENCE: 12

Glu Trp His Tyr Arg Leu Ser Ala
1 5

<210> SEQ ID NO 13
<211> LENGTH: 13
<212> TYPE: PRT
<213> ORGANISM: Avian Rotavirus D

<400> SEQUENCE: 13

Ser Asn His Val Pro Tyr Ile Phe Pro Tyr Asp Met Ala
1 5 10

<210> SEQ ID NO 14
<211> LENGTH: 11
<212> TYPE: PRT
<213> ORGANISM: Avian Rotavirus D

<400> SEQUENCE: 14

Ala Tyr Asp Arg Val Thr Ala Ala Tyr Asp Asn
1 5 10

<210> SEQ ID NO 15
<211> LENGTH: 13
<212> TYPE: PRT
<213> ORGANISM: Avian Rotavirus D

<400> SEQUENCE: 15

Leu Asn Asn Ala Ile His Phe Ala Ala Phe Asp Gln Asp
1 5 10

<210> SEQ ID NO 16
<211> LENGTH: 29
<212> TYPE: PRT
<213> ORGANISM: Avian Rotavirus D

<400> SEQUENCE: 16

Phe Glu Tyr Leu Tyr Asn Leu Arg Thr Pro Val Ser Asn Ala Thr Ile
1               5                   10                  15

Val Ile His Pro Ile Ser Ile Leu Ser Val Pro Ser Met
            20                  25

<210> SEQ ID NO 17
<211> LENGTH: 7
<212> TYPE: PRT
<213> ORGANISM: Avian rotavirus D

<400> SEQUENCE: 17

Ala Thr His Tyr Trp Pro Tyr
1               5

<210> SEQ ID NO 18
<211> LENGTH: 16
<212> TYPE: PRT
<213> ORGANISM: Avian Rotaviru D

<400> SEQUENCE: 18

Arg Val Glu Phe Gln Leu Ala Gly Gln Val Ile Tyr Val Ala Ala Asn
1               5                   10                  15

<210> SEQ ID NO 19
<211> LENGTH: 10
<212> TYPE: PRT
<213> ORGANISM: Avian Rotavirus D

<400> SEQUENCE: 19

Ile Pro Gln Phe Asp Ala Val Asn Ile Ile
1               5                   10

<210> SEQ ID NO 20
<211> LENGTH: 15
<212> TYPE: PRT
<213> ORGANISM: Avian Rotavirus D

<400> SEQUENCE: 20

Thr Met Arg Arg Leu Pro Leu Leu Ala Asp Leu Gln Asn Ile Phe
1               5                   10                  15

<210> SEQ ID NO 21
<211> LENGTH: 15
<212> TYPE: PRT
<213> ORGANISM: Avian Rotavirus D

<400> SEQUENCE: 21

Thr His Gln Ala Val Ile Ser Thr Lys Ile Glu Val Leu Asn Ala
1               5                   10                  15

<210> SEQ ID NO 22
<211> LENGTH: 15
<212> TYPE: PRT
<213> ORGANISM: Avian Rotavirus D

<400> SEQUENCE: 22

Thr Val Pro Ser Ile Asp Glu His Leu Tyr Ala Leu Ile Val Gly

<210> SEQ ID NO 23
<211> LENGTH: 8
<212> TYPE: PRT
<213> ORGANISM: Avian Rotavirus D

<400> SEQUENCE: 23

Gln Ala Gly Pro Val Phe Pro Pro
1               5

<210> SEQ ID NO 24
<211> LENGTH: 19
<212> TYPE: DNA
<213> ORGANISM: Artificial Sequence
<220> FEATURE:
<223> OTHER INFORMATION: primer

<400> SEQUENCE: 24
gcracaactg aracaacwg                                                19

<210> SEQ ID NO 25
<211> LENGTH: 19
<212> TYPE: DNA
<213> ORGANISM: Artificial Sequence
<220> FEATURE:
<223> OTHER INFORMATION: primer

<400> SEQUENCE: 25
ggaagcagtt gtcatcaac                                                19

<210> SEQ ID NO 26
<211> LENGTH: 30
<212> TYPE: DNA
<213> ORGANISM: Artificial Sequence
<220> FEATURE:
<223> OTHER INFORMATION: probe

<400> SEQUENCE: 26
ttgcatatta gattgtctcg ctggtgtata                                    30

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
ttagaaacca agctgccaca                                               20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
tgcaaatcag ctagcaatgg                                               20

<210> SEQ ID NO 29
<211> LENGTH: 20
<212> TYPE: DNA
<213> ORGANISM: Artificial Sequence
<220> FEATURE:

```
<223> OTHER INFORMATION: primer

<400> SEQUENCE: 29
tgccattgct agctgatttg                                          20

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
acgcatacca ggaggaaaga                                          20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
aaccaagctg ccacacacta                                          20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
tgcaaatcag ctagcaatgg                                          20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
aaaccaagct gccacacact                                          20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
aaaccaagct gccacacact                                          20

<210> SEQ ID NO 35
<211> LENGTH: 20
<212> TYPE: DNA
<213> ORGANISM: Artificial Sequence
<220> FEATURE:
<223> OTHER INFORMATION: primer

<400> SEQUENCE: 35
atttgaggac gccagtgtct                                          20
```

```
<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
atttgaggac gccagtgtct                                                    20
```